United States Patent [19]

Rodgers

[11] Patent Number: Plant 5,425

[45] Date of Patent: Apr. 2, 1985

[54] ROSE PLANT

[75] Inventor: Shafner R. Rodgers, Dallas, Tex.

[73] Assignee: Neiman-Marcus Company, Dallas, Tex.

[21] Appl. No.: 505,802

[22] Filed: Jun. 20, 1983

[51] Int. Cl.[3] ..... A01H 5/00

[52] U.S. Cl. ..... Plt/11

[58] Field of Search ..... Plt./11

*Primary Examiner*—Robert E. Bagwill

*Attorney, Agent, or Firm*—Vincent G. Gioia

[57] ABSTRACT

A new hybrid tea rose variety of generally pink blend which lightens upon aging.

2 Drawing Figures

1

The present invention relates to a new and distinct variety of rose plant of the hybrid tea rose class, which was originated by my crossing as seed parent the rose known as "Queen Elizabeth" (U.S. Plant Pat. No. 1,259) and the rose known as "Wind Sounds" as the pollen parent. The varietal denomination of the new rose is "Minnie Marcus".

Among the novel characteristics possessed by this new variety which distinguish it from its parents and all other varieties of which I am aware are flowers of delicate pink coloring beginning as Rhodamine Pink buds and lightening in pink tonality as petals unfurl. Outstanding features of the new variety are very vigorous plant growth habit; especially attractive glossy, leathery dark green foliage which is abundant and dense to the ground; and very floriferous blooming habit producing many flowers in typical hybrid tea fashion, one to a stem. The flowers are especially attractive in the fully open stage. Asexual reproduction by budding of the new variety as performed in Dallas County, Tex., shows that the foregoing and other distinguishing characteristics come true to form and are established and transmitted through succeeding propagations.

The accompanying drawings show typical specimens of the vegetative growth and flowers of the new variety in different stages of development and as depicted in color as nearly true as it is reasonably possible to make the same in a color illustration of this character.

Figure 1:
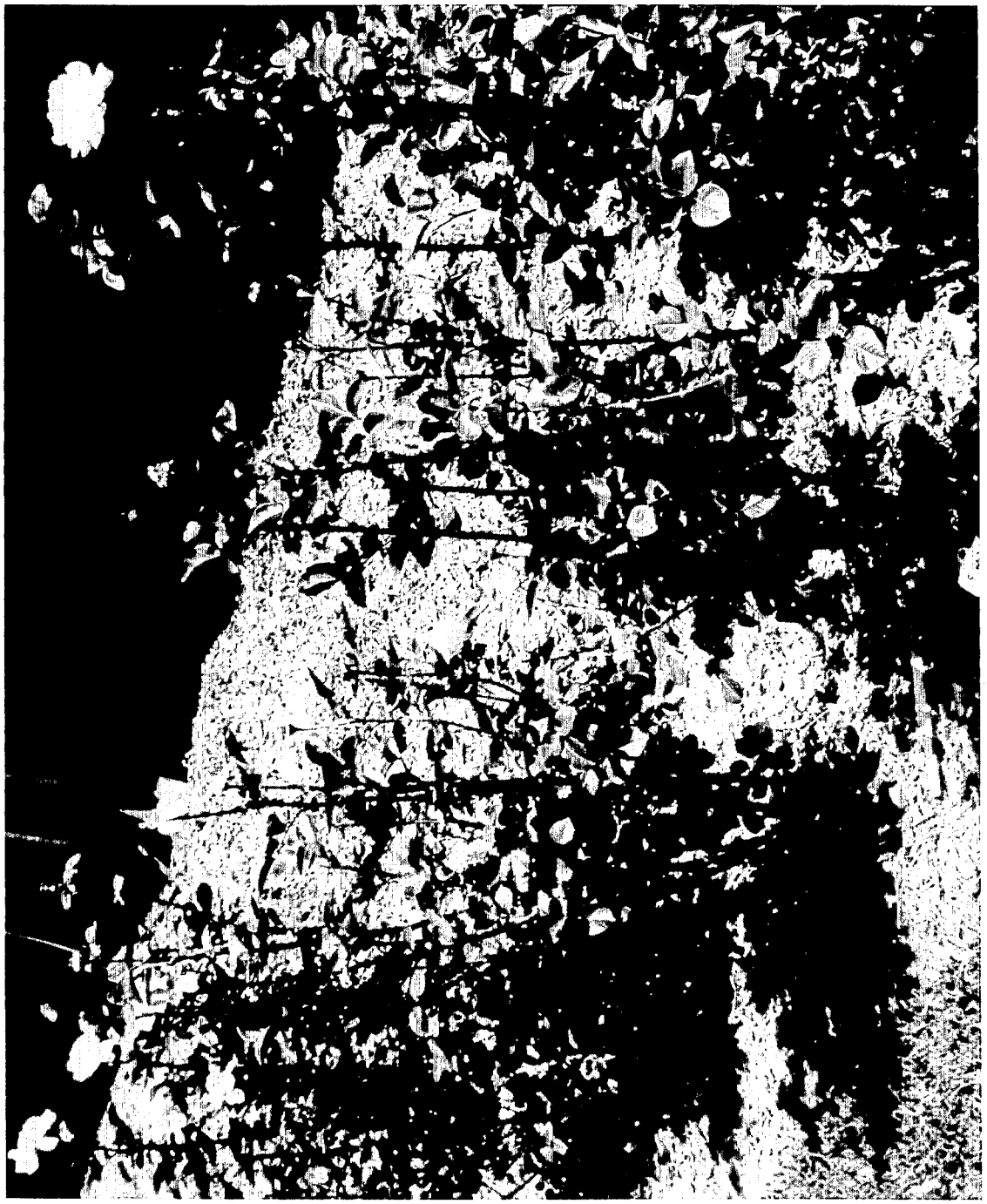
Figure 2:
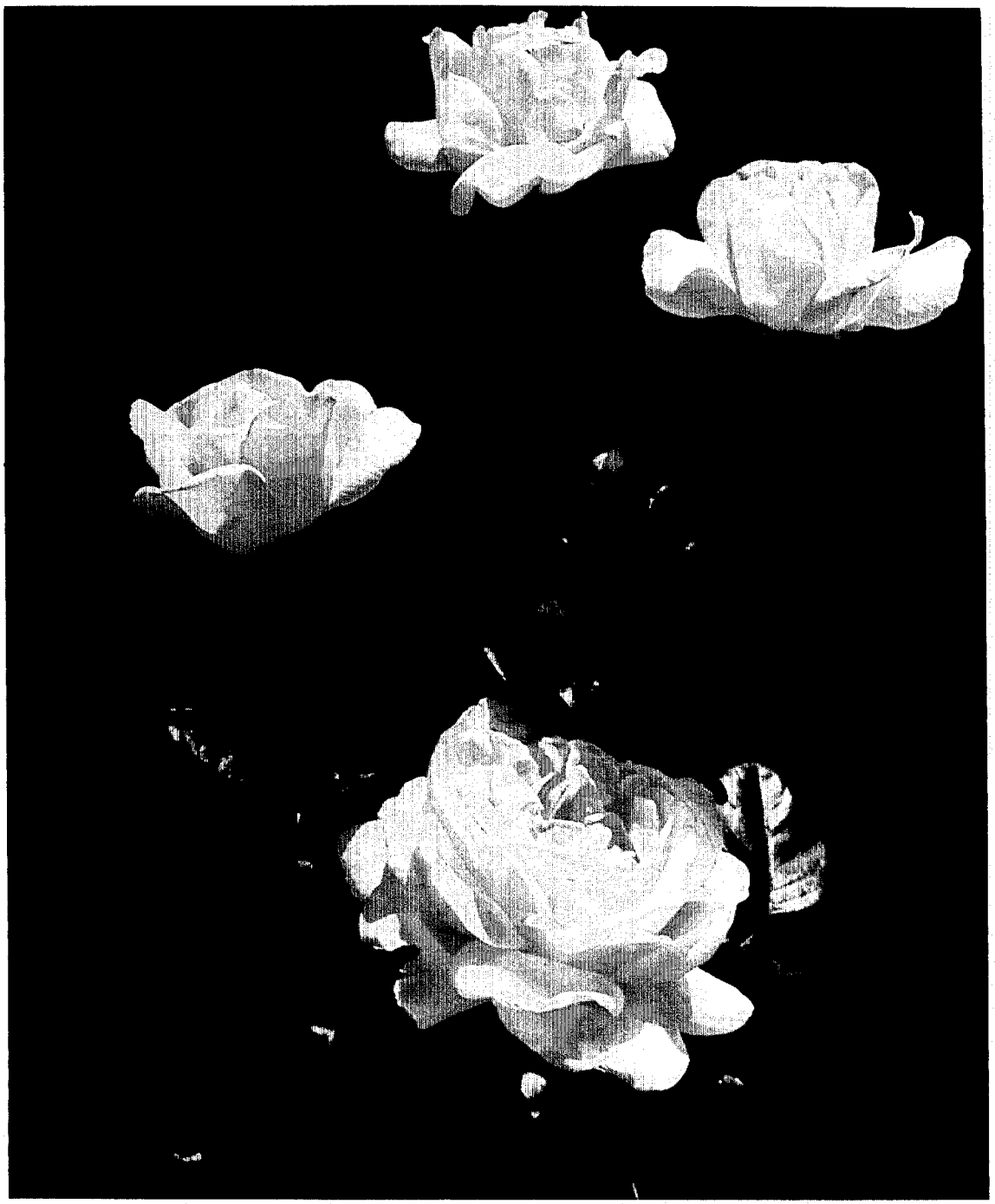

In the drawings, FIG. 1 is an illustration showing the robust habit of growth, the healthy-appearing, dark green glossy foliage, the blooming habit producing one bloom per stem and the substantial strength of stems and canes. FIG. 2 shows the form and color of the flowers.

The following is a detailed description of my new variety, with color terminology in accordance with The Royal Horticultural Society Colour Chart (R.H.S.C.C.). The terminology used in color description herein refers to plate numbers in the aforementioned color chart, e.g., "62A" is plate 62A of The Royal Horticultural Society Colour Chart.

Parentage: Seedling.

*Seed parent.*—"Queen Elizabeth".

*Pollen parent.*—"Wind Sounds".

Class: Hybrid Tea.

The following observations are made of specimens grown outdoors in Dallas County, Tex. during the months of September and October.

2

FLOWER

Blooming habit: Continuous, achieving five or more cycles of bloom in a growing season, an excellent garden rose variety.

Bud:

(1) *Size.*—Large.

(2) *Form.*—Ovoid.

(3) *Color.*—Buds are Rhodamine Pink 62A.

(4) *Sepals.*—Average length.

(5) *Peduncle.*—Length — medium to long. Aspect — straight. Strength — erect, strong. Color — reddish green.

Bloom:

(1) *Size.*—Average size when fully expanded — about 4½ to 5 inches.

(2) *Borne.*—Singly, one to a stem on strong peduncles.

(3) *Form.*—Cup-shaped opening flat.

(4) *Petalage.*—Number of petals under normal conditions — about 40 to 45.

(5) *Color.*—As sepals fall, Rhodamine Pink buds unfurl revealing the relatively deeper pink coloring of the petal undersurface in contrast to the lighter pink coloring of the petal top surface. The coloring of the petal undersurface ranges from 62A at the petal base lightening through the ranges of colors Phlox pink 62B to 62C and then to 62D near the petal edge. The deeper pink coloring of the petal undersurface tends to wash through the relatively thin petals producing the appearance of deeper pink washing or veining at the petal top surface which, but for the washing and veining, is essentially 62D. Occasional deeper pink coloring may be seen at some petal edges. As the bloom opens fully and ages, the inner petals tend to lighten in pink tonality almost to near white. However, where petals cluster, as in the flower center, the deeper pink tonality is more pronounced. The general tonality gives the appearance of a pink blend coloring.

Petals:

(1) *Texture.*—Thin, relatively soft substance.

(2) *Appearance.*—Both sides satiny with little color variation over entire surface.

(3) *Form.*—Wide, substantially fan-shaped.

(4) *Arrangement.*—Regular.

(5) *Petaloids in center.*—Many.

(6) *Persistence.*—Drop off cleanly.

(7) *Fragrance.*—Slight.

(8) *Lasting quality.*—Four to five days on plant and longer as cut flower.

REPRODUCTIVE ORGANS

Stamens, filaments and anthers:

(1) *Arrangement.*—Typical for species, regular arrangement, uneven length.

(2) *Color.*—Filaments yellow-orange.

Pollen:

*Color.*—Yellow-orange.

Styles: Tightly bunched, medium.

Stigmas: Small.

Hips:

*Shape.*—Ovoid.

*Size.*—Medium.

*Do seeds protrude?*—No.

PLANT

Form: Tall, upright.

Growth: Very vigorous, long stemmed.

*Height attained.*—About 5 to 6 feet.

Foliage: Compound, mostly 5 leaflets (1) *Size.*—Large.

(2) *Quantity.*—Abundant, dense to ground.

(3) *Color.*—New foliage. Upper side — reddish green. Under side — reddish green. Old foliage: Upper side — near 147A. Under side — near 147B.

(4) *Shape.*—Oval.

(5) *Texture.*—Upper side is shiny and glossy; under side is dull, both sides veined (6) *Edge.*—Serrate (7) *Serration.*—Simple, but heavy (8) *Leaf stem.*—Color — green with some reddish tonality.

(9) *Stipules.*—Relatively large.

(10) *Resistance to disease.*—Blackspot — good. Mildew — good.

Wood:

(1) *New wood.*—Color — reddish green maturing to 147D. Bark — smooth.

(2) *Old wood.*—Color — near 147C to 147B. Bark — smooth.

Thorns:

(1) *Thorns.*—Quantity (main stalk) — ordinary. On laterals from stalk — ordinary. Form — wide base, sometimes long. Length — varying size, large to medium. Position — irregular.

(2) *Prickles.*—Few.

Winter hardiness: Good winter hardiness.

I claim:

1. A new and distinct variety of rose plant of the hybrid tea class, substantially as shown and described, characterized particularly by a very vigorous plant with abundant, glossy, dark green foliage producing many large, cup-shaped pink blend flowers one to a stem on substantial stems.

* * * * *